(12) United States Patent
Jiang et al.

(10) Patent No.: US 12,739,549 B2
(45) Date of Patent: Sep. 15, 2026

(54) HANGING TYPE INTELLIGENT VOICE INPUT SYSTEM FOR ULTRASONIC REPORT

(71) Applicant: Tongji Hospital Affiliated to Tongji Medical College, Huazhong University of Science and Technology, Wuhan (CN)

(72) Inventors: Jingjing Jiang, Wuhan (CN); Xiaoyan Xu, Wuhan (CN); Xiao Wang, Wuhan (CN)

(73) Assignee: Tongji Hospital Affiliated to Tongji Medical College, Huazhong University of Science and Technology, Wuhan (CN)

( * ) Notice: Subject to any disclaimer, the term of this patent is extended or adjusted under 35 U.S.C. 154(b) by 0 days.

(21) Appl. No.: 19/260,225

(22) Filed: Jul. 3, 2025

(65) Prior Publication Data

US 2026/0113558 A1 Apr. 23, 2026

(30) Foreign Application Priority Data

Oct. 21, 2024 (CN) ......................... 202411476797.2

(51) Int. Cl.
*H04R 1/08* (2006.01)
*G06F 3/16* (2006.01)
*G16H 15/00* (2018.01)

(52) U.S. Cl.
CPC ............... *H04R 1/08* (2013.01); *G06F 3/167* (2013.01); *G16H 15/00* (2018.01)

(58) Field of Classification Search
CPC ... H04R 1/08; H04R 1/14; H04R 1/46; H04R 2201/107; H04R 5/0335; G16H 15/00; G06F 3/167
See application file for complete search history.

(56) References Cited

U.S. PATENT DOCUMENTS 9,955,248 B2 * 4/2018 Baek ........................ H04M 1/05
2017/0242659 A1 * 8/2017 Hörndl ................... H04R 1/026
2021/0258414 A1 * 8/2021 Nesterenko .......... H04R 1/1041
2025/0324184 A1 * 10/2025 Goh ....................... H04R 1/083

FOREIGN PATENT DOCUMENTS

CN 221149328 U 6/2024

* cited by examiner

*Primary Examiner* — Joseph Saunders, Jr.

(57) ABSTRACT

The present disclosure provides a hanging type intelligent voice input system for an ultrasonic report, including an adjustment module, collection modules and a control processing module. In the present disclosure, an arc-shaped back plate, fixing clamping plates, movable clamping plates, arc-shaped boxes, drawer boxes and voice boxes are wrapped around a neck in a ring, and distances between a mouth and the voice boxes are fixed, the situation of large and small voice input is not caused, the voice input is more accurate, the spoken voice is more concentrated in positions of the voice boxes, the environmental noise interference is less, it is unnecessary to input loudly to reduce the interference of ambient sound, and the input is more labor-saving.

10 Claims, 6 Drawing Sheets

HANGING TYPE INTELLIGENT VOICE INPUT SYSTEM FOR ULTRASONIC REPORT

CROSS-REFERENCE TO RELATED APPLICATION

This application claims priority of Chinese Patent Application No. 202411476797.2 filed on Oct. 21, 2024, the entire contents of which are incorporated herein by reference.

TECHNICAL FIELD

The present disclosure relates to the technical field of voice input, and in particular to a hanging type intelligent voice input system for an ultrasonic report.

BACKGROUND

Ultrasound examination generally refers to processing of imaging reflected waves by irradiating a body with sound waves, which can well reflect anatomical structures of various layers of tissues of the body, and normal ultrasound images of the body can be known and abnormal lesions can be found. At present, when performing ultrasound examination, it is usually performed by an ultrasound doctor and dictated and input into a report by an equipped typist, and sometimes input by a voice input equipment and converted into words.

The patent with an application number of 20232248156.3 provides "PORTABLE INTELLIGENT VOICE TRANSLATOR AND INTELLIGENT VOICE TRANSLATION SYSTEM", which has advantages of portability and easy operation, and can be widely used in travel, tourism, business and other scenes to improve communication efficiency and user experience. However, when inputting voice, a distance between an equipment and a mouth often changes due to actions of an operator, resulting in different input sound volumes and causing inaccurate input. Moreover, ambient sounds can also cause interference, further leading to inaccurate input sounds.

SUMMARY

The present disclosure provides a hanging type intelligent voice input system for an ultrasonic report, which can effectively solve the above-mentioned problems in the background that a distance between an equipment and a mouth often changes due to actions of an operator, resulting in different input sound volumes and causing inaccurate input. Moreover, ambient sounds can also cause interference, further leading to inaccurate input sounds.

In order to achieve the above objective, the present disclosure provides the following technical solutions. A hanging type intelligent voice input system for an ultrasonic report includes an arc-shaped back plate. The arc-shaped back plate is mounted with a precise sound recording assembly, and the precise sound recording assembly includes fixing clamping plates;

two ends of the arc-shaped back plate are fixedly connected to the fixing clamping plates, ends of the fixing clamping plates are disposed with rotating grooves, and movable clamping plates are rotatably mounted in the rotating grooves; ends of the movable clamping plates are welded with arc-shaped boxes, drawer boxes are slidably mounted in the arc-shaped boxes, and ends of the arc-shaped boxes close to the drawer boxes are bonded with rubber rings; piston strips are slidably mounted at bottom ends inside the drawer boxes, sealing rings are sleeved on outer sides of the piston strips, sound insulation plates are bonded to top surfaces of the piston strips; and support strips are uniformly distributed on sides of the sound insulation plates, nano silver films are bonded to the other sides of the sound insulation plates, and sealing top plates are bonded to top ends of the sound insulation plates; and voice boxes are welded to ends of the drawer boxes, soft magnetic strips are bonded to sides of the voice boxes away from the drawer boxes, a magnetic attraction groove is formed in a middle of one of the soft magnetic strips, and a magnetic attraction strip is embedded in the other one of the soft magnetic strips corresponding to the magnetic attraction groove; guide tubes are welded to adjacent sides of the voice boxes and the soft magnetic strips, aluminum strips are slidably mounted inside the guide tubes, right-angle plates are mounted at bottom ends of the aluminum strips, and suction cups are embedded in middles of the right-angle plates; and a battery box is mounted in a middle of a back surface of the arc-shaped back plate.

According to the above technical solution, rotating shafts are fixedly mounted inside the rotating grooves, the movable clamping plates are movably sleeved on outer sides of the rotating shafts, ends of the rotating shafts are movably clamped with extrusion cover plates, and sides of the extrusion cover plates close to the movable clamping plates are rough planes.

According to the above technical solution, pressure equalizing holes are disposed at bottom ends of the arc-shaped boxes close to the movable clamping plates, communication holes are disposed at bottom ends of the drawer boxes close to the arc-shaped boxes, and pick-up grooves are disposed at middles of top ends of the drawer boxes.

According to the above technical solution, bottom ends of the aluminum strips are curved in semicircular shapes, outer sides of the aluminum strips are wrapped with polytetrafluoroethylene protective films, cross sections of the guide tubes are hollow rectangles, and the outer sides of the aluminum strips are attached to inner walls of the guide tubes.

According to the above technical solution, auxiliary adjustment assemblies are mounted on the arc-shaped back plate and the fixing clamping plates, and the auxiliary adjustment assemblies include mounting grooves;

mounting grooves are disposed in middles of the fixing clamping plates, and folding airbags are embedded inside the mounting grooves; air-filling and suction dual-purpose air pumps penetrate through and are mounted in the middles of the fixing clamping plates, and inflation ends of the air-filling and suction dual-purpose air pumps are connected to the folding airbags; and flexible ventilation tubes are mounted at bottom ends of the fixing clamping plates, ends of the flexible ventilation tubes are connected to the folding airbags, and the other ends of the flexible ventilation tubes are connected to the pressure equalizing holes;

magnets are embedded at the bottom ends of the fixing clamping plates, flexible sliding sleeves are slidably sleeved in middles of the flexible ventilation tubes, and iron sheets are bonded to bottom ends of the flexible sliding sleeves; cushion plates are bonded to sides of the folding airbags, closed grooves are disposed at bottom ends of the cushion plates, and ventilation holes are disposed at top ends of the folding airbags corresponding to the closed grooves; and closed strips are slidably clamped in the closed grooves, the plurality of closed strips are all connected to top surfaces of pulling plates, and cushion blocks are uniformly bonded to sides of the cushion plates; and a buffer box is bonded to a middle part of the arc-shaped back plate, adjusting holes are disposed in a middle part of one side and two ends of the buffer box, and folding rubber tubes are bonded inside the adjusting holes; elastic net cages are bonded to sides of the folding rubber tubes inside the buffer box, and breather holes are evenly disposed in the folding rubber tubes close to the elastic net cages; an internally threaded tube is rotatably mounted in the middle part of the arc-shaped back plate, and one end of the internally threaded tube penetrating through the buffer box is connected to a threaded rod through threads; and one end of the threaded rod is located inside the buffer box and is connected to a push plate by welding, and buffer springs are evenly distributed between the push plate and the elastic net cages.

According to the above technical solution, protective top plates are bonded to top surfaces of the folding airbags, traditional Chinese medicine bags are filled inside the elastic net cages, and an end cap is movably clamped at a top end of the buffer box.

According to the above technical solution, input ends of the voice boxes and the air-filling and suction dual-purpose air pumps are electrically connected to output ends of an external controller, and an input end of the controller is electrically connected to an output end of the battery box.

According to the above technical solution, the system includes an adjustment module, collection modules and a control processing module;

the adjustment module includes the arc-shaped boxes, the drawer boxes, the piston strips, the folding airbags, the air-filling and suction dual-purpose air pumps and the flexible ventilation tubes;

the collection modules are the voice boxes; and the control processing module is the external controller, and the external controller can be connected to wireless fidelity (WiFi) and Bluetooth for wireless operation.

According to the above technical solution, the adjustment module includes adjusting steps of:

inflating the folding airbags by the air-filling and suction dual-purpose air pumps, inflating the arc-shaped boxes through the flexible ventilation tubes, pushing the drawer boxes to slide along the arc-shaped boxes and eject, and allowing air to enter bottom ends of the drawer boxes to eject the piston strips.

According to the above technical solution, voice input by the collection modules is compared with online medical professional vocabulary data through the external controller, and the medical professional vocabulary is combined and input into a report.

Compared with the related art, the present disclosure has the following beneficial effects.

1. By arranging the precise sound recording assembly, the movable clamping plates in the rotating grooves are rotated to make the two voice boxes face each other and close to two sides of the mouth, the aluminum strips in the guide tubes are drawn and bent into arc shapes, the right-angle plates are close to a chin position, and the folding rubber tubes and the right-angle plates are used to fix the front and rear positions of the neck. The sound insulation plates are raised slowly, when the soft magnetic strips of the two voice boxes are close to each other, the magnetic attraction groove and the magnetic attraction strip are attracted to each other, and the suction cups are attracted to the chin for fixing to clamp and fix, and the sound insulation plates are prevented from being completely pushed out of the drawer boxes. The arc-shaped back plate, the fixing clamping plates, the movable clamping plates, the arc-shaped boxes, the drawer boxes and the voice boxes are wrapped around the neck in a ring, and distances between the mouth and the voice boxes are fixed, the situation of large and small voice input is not caused, and the voice input is more accurate.

A front of the mouth is blocked by the drawer boxes, the sound insulation plates and the voice boxes, the nano silver films have strong antibacterial ability, the spoken voice is more concentrated in the positions of the voice boxes, and the interference of the ambient sound is less; and it is not necessary to input loudly to reduce the interference of the ambient sound, but only rely on ordinary whispers, and input is more labor-saving.

2. By arranging the auxiliary adjustment assemblies. When the internally threaded tube is rotated, the threaded rod is pushed, and at the same time, the push plate will push the buffer springs; and the folding rubber tubes are unfolding, the sides of the elastic net cages of the folding rubber tubes are close to the rear neck position, and the positioning effect of the device is better when wearing, further reducing the shaking of the device.

If the device needs to be used and worn for a long time, the end cap can be opened, and the traditional Chinese medicine bags can be placed in the elastic net cages. The traditional Chinese medicine bags are filled with Moschus, Lignum Aquilariae Resinatum, Borneolum Syntheticum, Herba Menthae and other medicines with refreshing effects, and the smell exudes through the ventilation holes. The air-filling and suction dual-purpose air pumps are started again, and the pulling plates are pulled to drive the closed strips to slide in the closed grooves. The ventilation holes are opened, the air is ejected from the ventilation holes and flows to a periphery of the neck along gaps between the cushion blocks to accelerate the evaporation of sweat. In cooperation with the smell emitted from the traditional Chinese medicine bags, the comfort of wearing is improved, which is more conducive to voice input.

3. The precise sound recording assembly in the positioning adjustment process can also be completely performed manually, the movable clamping plates and the drawer boxes are pulled in sequence, the sealing top plates and the sound insulation plates are drawn out from the pick-up grooves, and the magnetic attraction groove and the magnetic attraction strip are butted to complete the positioning operation. With the auxiliary adjustment assemblies, the automatic fixing operation can be completed by the external controller of the system, and the operation can be selected by itself as needed to further improve the convenience of the operation. The voice input by the collection modules in the voice boxes are compared with online medical professional vocabulary data through the external controller, the medical professional vocabulary is combined and input into a report, and matched with the precise sound recording assembly to further improve the accuracy of the entry.

BRIEF DESCRIPTION OF THE DRAWINGS

The accompanying drawings, which are included to provide a further understanding of the present disclosure and constitute a part of this specification, illustrate embodiments of the present disclosure and together with the description serve to explain the present disclosure and are not to be construed as limiting the present disclosure.

In the accompanying drawings.

Figure 1:
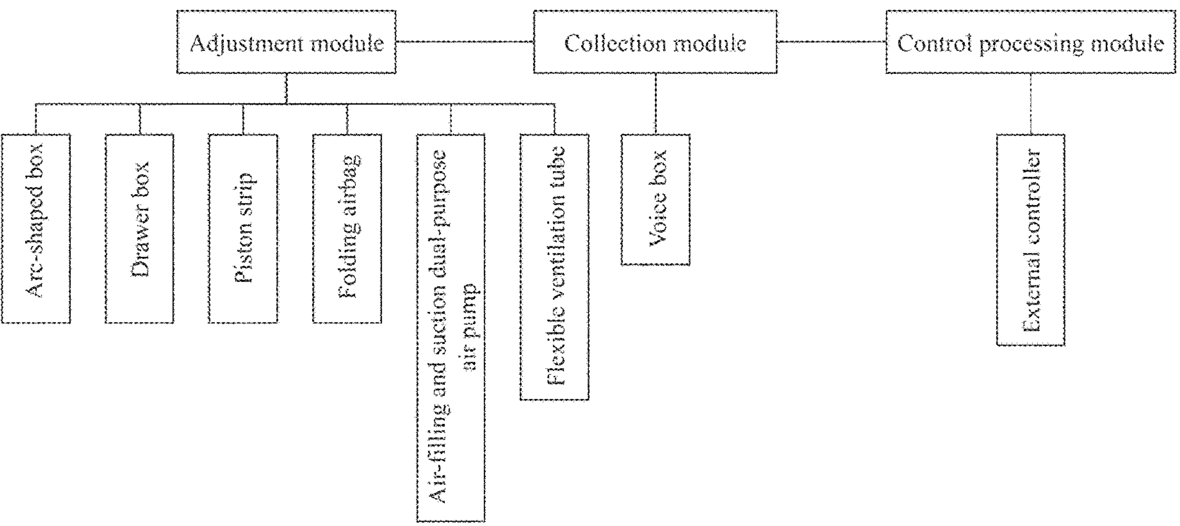
FIG. 1 is a schematic diagram of a system of the present disclosure.

Reference numerals and denotations thereof: 1—arc-shaped back plate;

- 2—precise sound recording assembly; 201—fixing clamping plate; 202—rotating groove; 203—movable clamping plate; 204—rotating shaft; 205—extrusion cover plate; 206—arc-shaped box; 207—drawer box; 208—rubber ring; 209—pressure equalizing hole; 210—communication hole; 211—piston strip; 212—sealing ring; 213—sound insulation plate; 214—support strip; 215—nano silver film; 216—sealing top plate; 217—voice box; 218—soft magnetic strip; 219—magnetic attraction groove; 220—magnetic attraction strip; 221—guide tube; 222—aluminum strip; 223—right-angle plate; 224—suction cup; 225—battery box; and 226—pick-up groove; and
- 3—auxiliary adjustment assembly; 301—mounting groove; 302—folding airbag; 303—air-filling and suction dual-purpose air pump; 304—flexible ventilation tube; 305—magnet; 306—flexible sliding sleeve; 307—iron sheet; 308—cushion plate; 309—closed groove; 310—ventilation hole; 311—closed strip; 312—pulling plate; 313—cushion block; 314—buffer box; 315—adjusting hole; 316—folding rubber tube; 317—elastic net cage; 318—breather hole; 319—internally threaded tube; 320—threaded rod; 321—push plate; 322—buffer spring; 323—protective top plate; 324—traditional Chinese medicine bag; 325—end cap.

DETAILED DESCRIPTION

While the preferred examples of the present disclosure will be described below with reference to the accompanying drawings, and it is to be understood that the preferred examples described herein are illustrative and explanatory only and are not restrictive.

Examples: as shown in FIG. 1, the present disclosure provides a technical solution of a hanging type intelligent voice input system for an ultrasonic report, including an adjustment module, collection modules and a control processing module;

- the adjustment module includes arc-shaped boxes 206, drawer boxes 207, piston strips 211, folding airbags 302, air-filling and suction dual-purpose air pumps 303 and flexible ventilation tubes 304;
- the collection modules are the voice boxes 217; and
- the control processing module is the external controller, and the external controller can be connected to WiFi and Bluetooth for wireless operation.

According to the above technical solution, the adjustment module includes the following adjusting steps.

Air is inflated into the folding airbags 302 by the air-filling and suction dual-purpose air pumps 303, and inflated into the arc-shaped boxes 206 through the flexible ventilation tubes 304. The drawer box 207 are pushed to slide along the arc-shaped boxes 206 and eject, and the air enters bottom ends of the drawer boxes 207 to eject the piston strips 211.

According to the above technical solution, voice input by the collection modules is compared with online medical professional vocabulary data through the external controller, and the medical professional vocabulary is combined and input into a report.

As shown in FIGS. 2-10, an arc-shaped back plate 1 is mounted with a precise sound recording assembly 2, and the precise sound recording assembly 2 includes fixing clamping plates 201, rotating grooves 202, movable clamping plates 203, rotating shafts 204, extrusion cover plates 205, the arc-shaped boxes 206, the drawer boxes 207, rubber rings 208, pressure equalizing holes 209, communication holes 210, the piston strips 211, sealing rings 212, sound insulation plates 213, support strips 214, nano silver films 215, sealing top plates 216, the voice boxes 217, soft magnetic strips 218, a magnetic attraction groove 219, a magnetic attraction strip 220, guide tubes 221, aluminum strips 222, right-angle plates 223, suction cups 224, a battery box 225 and pick-up grooves 226.

Two ends of the arc-shaped back plate 1 are fixedly connected to the fixing clamping plates 201, ends of the fixing clamping plates 201 are disposed with the rotating grooves 202, and the movable clamping plates 203 are rotatably mounted in the rotating grooves 202; the rotating shafts 204 are fixedly mounted inside the rotating grooves 202, the movable clamping plates 203 are movably sleeved on outer sides of the rotating shafts 204, ends of the rotating shafts 204 are movably clamped with the extrusion cover plates 205, and sides of the extrusion cover plates 205 close to the movable clamping plates 203 are rough planes, which is convenient for the movable clamping plates 203 to be temporarily positioned by friction; ends of the movable clamping plates 203 are welded with the arc-shaped boxes 206, the drawer boxes 207 are slidably mounted in the arc-shaped boxes 206, ends of the arc-shaped boxes 206 close to the drawer boxes 207 are bonded with rubber rings 208, and the piston strips 211 are slidably mounted at bottom ends inside the drawer boxes 207; the pressure equalizing holes 209 are disposed at bottom ends of the arc-shaped boxes 206 close to the movable clamping plates 203, the communication holes 210 are disposed at bottom ends of the drawer boxes 207 close to the arc-shaped boxes 206, and the pick-up grooves 226 are disposed at middles of top ends of the drawer boxes 207, which balances the air pressure and facilitates the movement of the drawer boxes 207 and the piston strips 211; and the sealing rings 212 are sleeved on outer sides of the piston strips 211, the sound insulation plates 213 are bonded to top surfaces of the piston strips 211; and the support strips 214 are uniformly distributed on sides of the sound insulation plates 213, the nano silver films 215 are bonded to the other sides of the sound insulation plates 213, and the sealing top plates 216 are bonded to top ends of the sound insulation plates 213.

The voice boxes 217 are welded to ends of the drawer boxes 207, the soft magnetic strips 218 are bonded to sides of the voice boxes 217 away from the drawer boxes 207, the magnetic attraction groove 219 is formed in a middle of one of the soft magnetic strips 218, and the magnetic attraction strip 220 is embedded in the other one of the soft magnetic strips 218 corresponding to the magnetic attraction groove 219; the guide tubes 221 are welded to adjacent sides of the voice boxes 217 and the soft magnetic strips 218, and the aluminum strips 222 are slidably mounted inside the guide tubes 221; bottom ends of the aluminum strips 222 are curved in semicircular shapes, outer sides of the aluminum strips 222 are wrapped with polytetrafluoroethylene protective films, cross sections of the guide tubes 221 are hollow rectangles, the outer sides of the aluminum strips 222 are attached to inner walls of the guide tubes 221, and the aluminum strips 222 can be temporarily movably clamped in the guide tubes 221; the right-angle plates 223 are mounted at bottom ends of the aluminum strips 222, and the suction cups 224 are embedded in middles of the right-angle plates 223; and the battery box 225 is mounted in a middle of a back surface of the arc-shaped back plate 1.

The arc-shaped back plate 1 and the fixing clamping plates 201 are mounted with auxiliary adjustment assemblies 3, and the auxiliary adjustment assemblies 3 include mounting grooves 301, the folding airbags 302, the air-filling and suction dual-purpose air pumps 303, the flexible ventilation tubes 304, magnets 305, flexible sliding sleeves 306, iron sheets 307, cushion plates 308, closed grooves 309, ventilation holes 310, closed strips 311, pulling plates 312, cushion blocks 313, buffer box 314, adjusting holes 315, folding rubber tubes 316, elastic net cages 317, breather holes 318, internally threaded tube 319, threaded rod 320, push plate 321, buffer springs 322, protective top plates 323, traditional Chinese medicine bags 324, and end cap 325.

The mounting grooves 301 are disposed in middles of the fixing clamping plates 201, and the folding airbags 302 are embedded inside the mounting grooves 301; the air-filling and suction dual-purpose air pumps 303 penetrate through and are mounted in the middles of the fixing clamping plates 201, input ends of the voice boxes 217 and the air-filling and suction dual-purpose air pumps 303 are electrically connected to output ends of an external controller, and an input end of the controller is electrically connected to an output end of the battery box 225 to ensure that the voice boxes 217 and the air-filling and suction dual-purpose air pumps 303 can work normally; inflation ends of the air-filling and suction dual-purpose air pumps 303 are connected to the folding airbags 302, the flexible ventilation tubes 304 are mounted at bottom ends of the fixing clamping plates 201, ends of the flexible ventilation tubes 304 are connected to the folding airbags 302, and the other ends of the flexible ventilation tubes 304 are connected to the pressure equalizing holes 209; the magnets 305 are embedded at the bottom ends of the fixing clamping plates 201, the flexible sliding sleeves 306 are slidably sleeved in middles of the flexible ventilation tubes 304, and the iron sheets 307 are bonded to bottom ends of the flexible sliding sleeves 306; the cushion plates 308 are bonded to sides of the folding airbags 302, the closed grooves 309 are disposed at bottom ends of the cushion plates 308, and the ventilation holes 310 are disposed at top ends of the folding airbags 302 corresponding to the closed grooves 309; and the closed strips 311 are slidably clamped in the closed grooves 309, the plurality of closed strips 311 are all connected to top surfaces of pulling plates 312, and the cushion blocks 313 are uniformly bonded to sides of the cushion plates 308.

The buffer box 314 is bonded to a middle part of the arc-shaped back plate 1, the adjusting holes 315 are disposed in a middle part of one side and two ends of the buffer box 314, and the folding rubber tubes 316 are bonded inside the adjusting holes 315; the elastic net cages 317 are bonded to sides of the folding rubber tubes 316 inside the buffer box 314, and the breather holes 318 are evenly disposed in the folding rubber tubes 316 close to the elastic net cages 317; the internally threaded tube 319 is rotatably mounted in the middle part of the arc-shaped back plate 1, and one end of the internally threaded tube 319 penetrating through the buffer box 314 is connected to the threaded rod 320 through threads; and one end of the threaded rod 320 is located inside the buffer box 314 and is connected to the push plate 321 by welding, and the buffer springs 325 are evenly distributed between the push plate 321 and the elastic net cages 317. The protective top plates 323 are bonded to top surfaces of the folding airbags 302, the traditional Chinese medicine bags 324 are filled inside the elastic net cages 317, and the end cap 325 is movably clamped at a top end of the buffer box 314, which improves the convenience of the device.

Working principle and use process of the present disclosure are as follows. The arc-shaped back plate 1 is picked up, the fixing clamping plates 201 are pulled by two hands, the arc-shaped back plate 1 is close to a back neck position, the device is put on the neck position, the movable clamping plates 203 in the rotating grooves 202 are rotated, and the two voice boxes 217 are opposite and close to two sides of the mouth. When the internally threaded tube 319 is rotated, the threaded rod 320 is pushed, and at the same time, the push plate 321 pushes the buffer springs 322 to expand the folding rubber tubes 316. Sides of the elastic net cages 317 of the folding rubber tubes 316 are close to the back neck position, the aluminum strips 222 in the guide tubes 221 are drawn and bent into arc shapes, and the right-angle plates 223 are close to a chin position. The folding rubber tubes 316 and the right-angle plates 223 are used to fix the front and rear positions of the neck to ensure that positions of the voice boxes 217 and the mouth are fixed, which is not easy to be changed due to the activities of operators, and the stability of voice input is improved. Moreover, the above manual operation and positioning process only needs to be changed once at the same operator, and no adjustment is needed for the next use.

Figure 2:
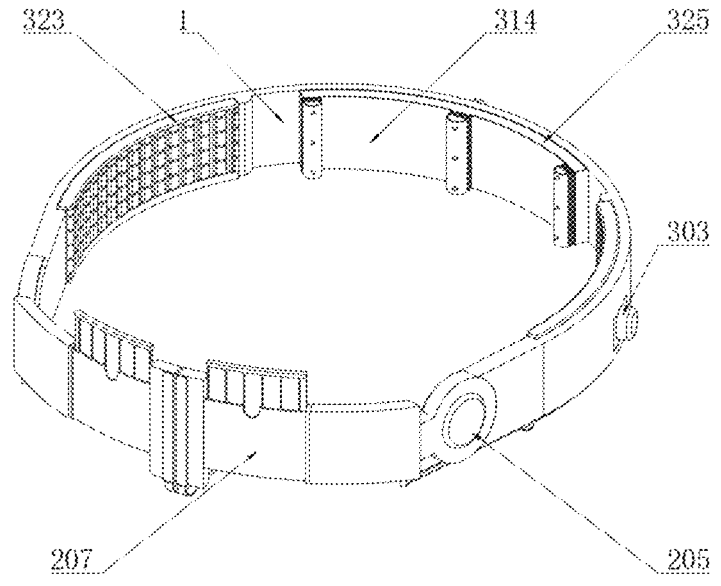
FIG. 2 is a schematic structural diagram of the present disclosure.
Figure 3:
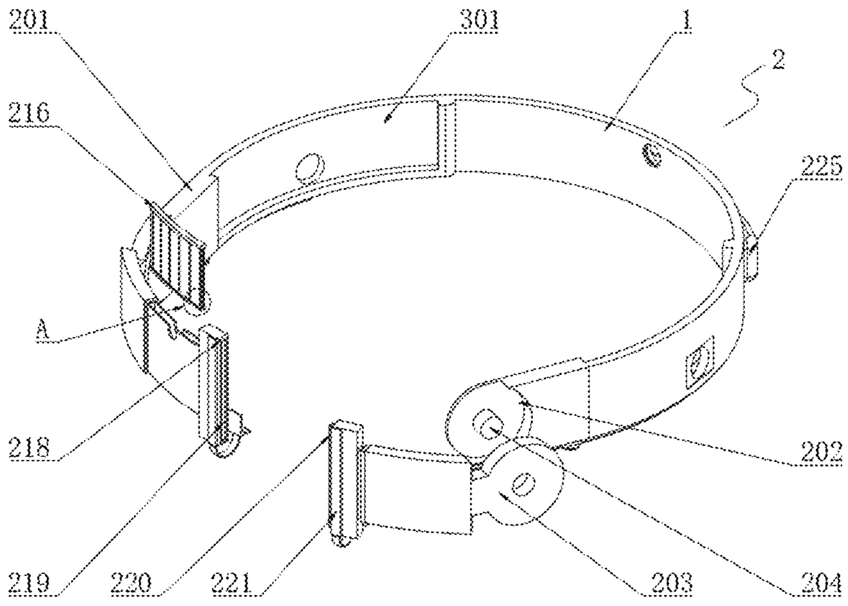
FIG. 3 is a schematic structural diagram of a precise sound recording assembly of the present disclosure.
Figure 4:
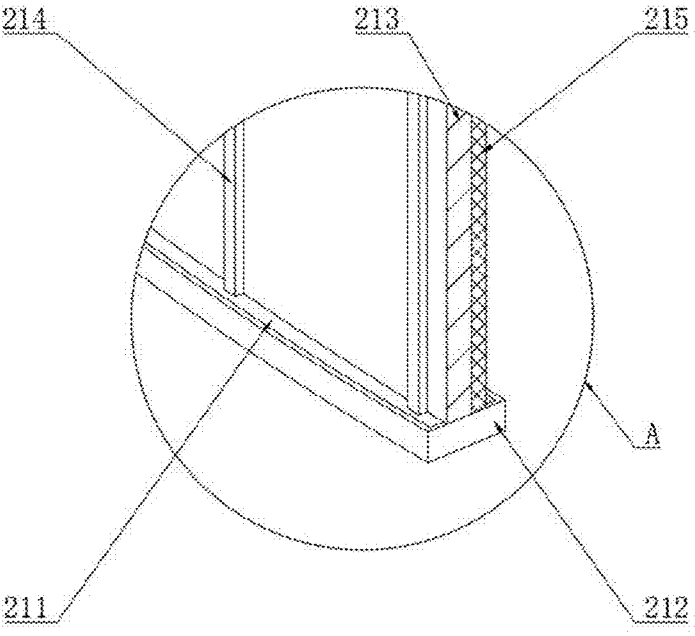
FIG. 4 is a schematic structural diagram of a region A in FIG. 3 of the present disclosure.
Figure 5:
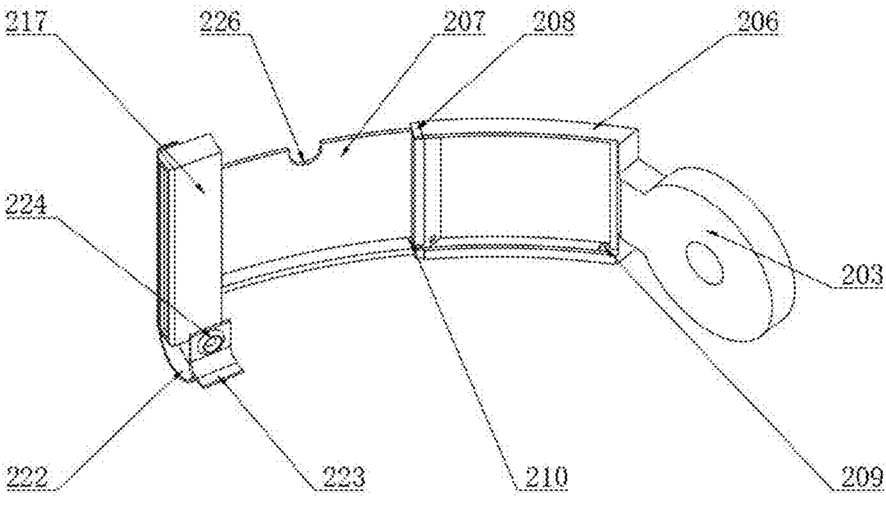
FIG. 5 is a schematic diagram of a mounting structure of voice boxes of the present disclosure.
Figure 6:
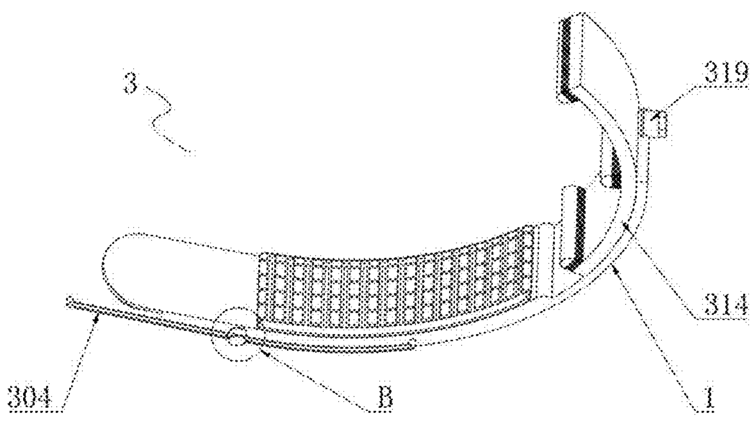
FIG. 6 is a schematic structural diagram of auxiliary adjustment assemblies of the present disclosure.
Figure 7:
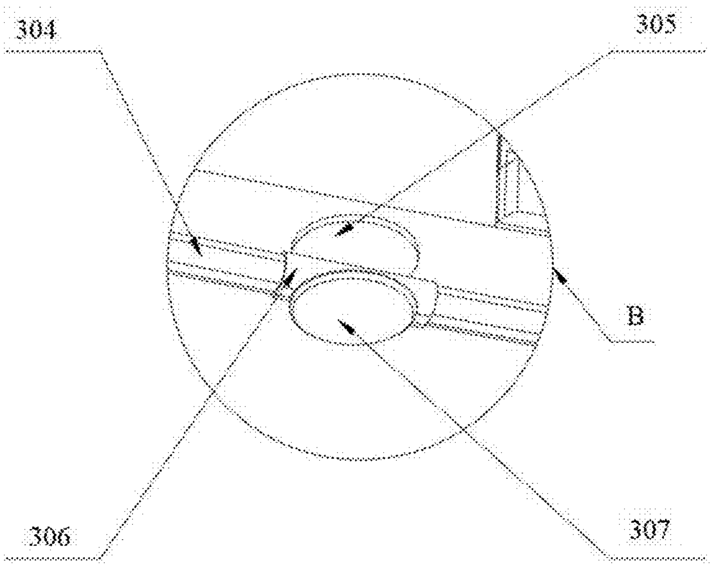
FIG. 7 is a schematic structural diagram of a region B in FIG. 6 of the present disclosure.
Figure 8:
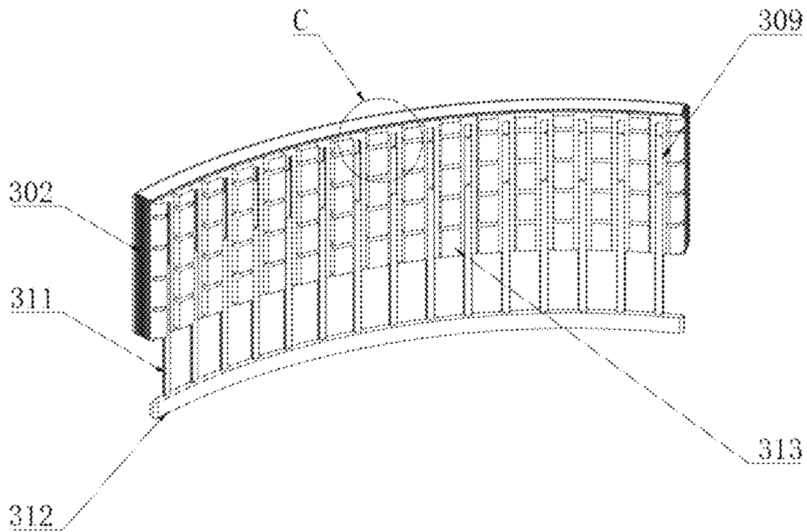
FIG. 8 is a schematic diagram of a mounting structure of closed strips of the present disclosure.
Figure 9:
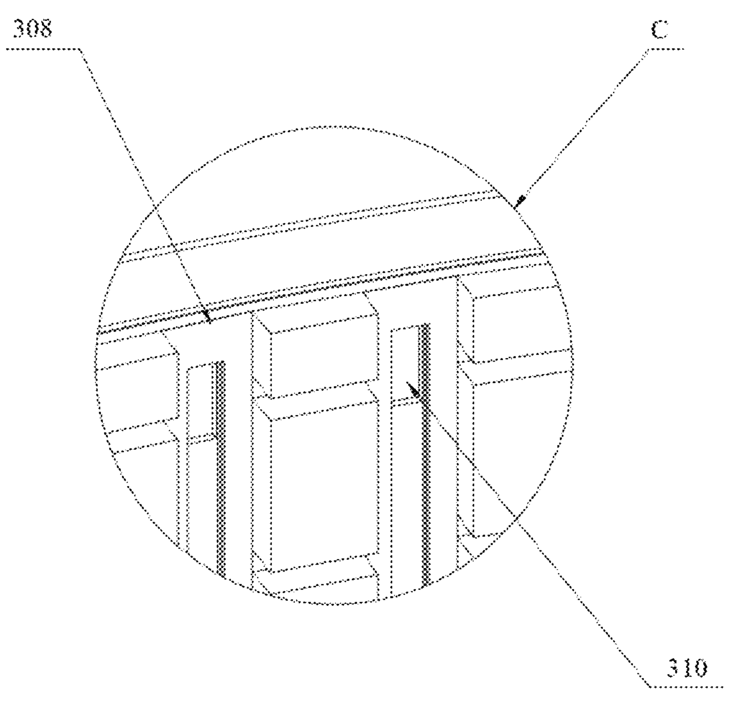
FIG. 9 is a schematic structural diagram of a region C in FIG. 8 of the present disclosure.
Figure 10:
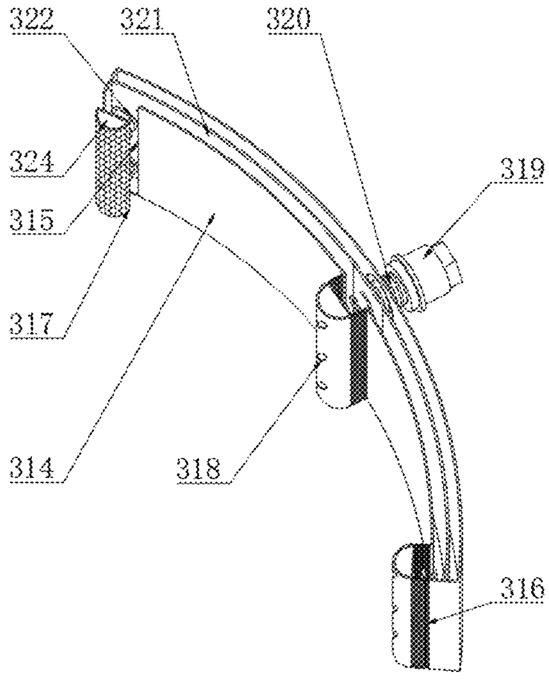
FIG. 10 is a schematic diagram of a mounting structure of folding rubber tubes of the present disclosure.

The flexible sliding sleeves 306 are pulled along the flexible ventilation tubes 304, and the magnets 305 and the iron sheets 307 are separated; and the air-filling and suction dual-purpose air pumps 303 are started, the air is inflated into the folding airbags 302 by the air-filling and suction dual-purpose air pumps 303 and inflated into the arc-shaped boxes 206 through the flexible ventilation tubes 304 and the pressure equalizing holes 209, the drawer boxes 207 are pushed to eject along the arc-shaped boxes 206. After the sealing top plates 216 are no longer blocked by the arc-shaped boxes 206, the air enters the bottom ends of the drawer boxes 207 through the communication holes 210, and the piston strips 211 are ejected to slowly rise the sound insulation plates 213. When the soft magnetic strips 218 of the two voice boxes 217 are close to each other, the magnetic attraction groove 219 and the magnetic attraction strip 220 are attracted to each other, and the suction cups 224 are attracted to the chin for fixing. As the folding airbags 302 inflates, the folding airbags 302 pushes the cushion blocks 313 to be close to the two sides of the neck for clamping and fixing. With the front and rear positioning of the neck, the device is less likely to loosen. The flexible sliding sleeves 306 sleeved on the flexible ventilation tubes 304 are pulled, the magnets 305 and the iron sheets 307 are attracted to each other, and the flexible sliding sleeves 306 are squeezed and closed. To prevent the sound insulation plates 213 from being completely pushed out of the drawer boxes 207, the arc-shaped back plate 1, the fixing clamping plates 201, the movable clamping plates 203, the arc-shaped boxes 206, the drawer boxes 207 and the voice boxes 217 form a ring around the neck, and the above structure is shown in FIG. 2.

The precise sound recording assembly 2 in the above adjustment process can also be completely performed manually, the movable clamping plates 203 and the drawer boxes 207 are pulled in sequence, the sealing top plates 216 and the sound insulation plates 213 are drawn out from the pick-up grooves 226, and the magnetic attraction groove 219 and the magnetic attraction strip 220 are butted to complete the positioning operation. With the auxiliary adjustment assemblies 3, semi-automatic fixing operation can be achieved, and the operation can be selected by itself as needed to further improve the convenience of the operation. The voice input by the collection modules in the voice boxes 217 are compared with online medical professional vocabulary data through the external controller, the medical professional vocabulary is combined and input into a report, and matched with the precise sound recording assembly to further improve the accuracy of the entry.

During the voice input, the front of the mouth is blocked by the drawer boxes 207, the sound insulation plates 213 and the voice boxes 217, the nano silver films 215 have strong antibacterial ability, the spoken voice is more concentrated in the positions of the voice boxes 217, and the interference of the ambient sound is less; and it is not necessary to input loudly to reduce the interference of the ambient sound, but only rely on ordinary whispers, and input is more labor-saving.

If the device needs to be used and worn for a long time, the end cap 325 can be opened, and the traditional Chinese medicine bags 324 can be placed in the elastic net cages 317. The traditional Chinese medicine bags 324 are filled with Moschus, Lignum Aquilariae Resinatum, Borneolum Syntheticum, Herba Menthae and other medicines with refreshing effects, and the smell exudes through the breather holes 318. The air-filling and suction dual-purpose air pumps 303 are started again, and the pulling plates 312 are pulled to drive the closed strips 311 to slide in the closed grooves 309. The ventilation holes 310 are opened, the air is ejected from the ventilation holes 310 and flows to a periphery of the neck along gaps between the cushion blocks 313 to accelerate the evaporation of sweat. In cooperation with the smell emitted from the traditional Chinese medicine bags 324, the comfort of wearing is improved, which is more conducive to voice input.

After the voice input is completed, the two soft magnetic strips 218 attracted to each other are separated, the flexible sliding sleeves 306 are pulled along the flexible ventilation tubes 304, and the magnets 305 and the iron sheets 307 are disengaged. The air-filling and suction dual-purpose air pumps 303 are started to extract the air in the folding airbags 302, the arc-shaped boxes 206 and the drawer boxes 207. After the piston stripe 211 retract to the bottom ends of the drawer boxes 207 under the action of air pressure, the drawer boxes 207 will also automatically retract to the arc-shaped boxes 206, and the device is removed for the next use, which is convenient to use.

Finally, it is to be noted that the above description is merely a preferred example of the present disclosure and is not intended to limit the present disclosure. Although the present disclosure has been described in detail with reference to the foregoing examples, those skilled in the art can still modify the technical solutions described in the foregoing examples, or make equivalent replacements to some technical features thereof. Any modifications, equivalent replacements, and improvements made within the spirit and principle of the present disclosure are included in the protection scope of the present disclosure.

The invention claimed is:

1. A hanging type intelligent voice input system for an ultrasonic report, comprising an arc-shaped back plate (1), wherein a precise sound recording assembly (2) is mounted on the arc-shaped back plate (1), and the precise sound recording assembly (2) comprises fixing clamping plates (201);

two ends of the arc-shaped back plate (1) are fixedly connected to the fixing clamping plates (201), ends of the fixing clamping plates (201) are disposed with rotating grooves (202), and movable clamping plates (203) are rotatably mounted in the rotating grooves (202); ends of the movable clamping plates (203) are welded with arc-shaped boxes (206), drawer boxes (207) are slidably mounted in the arc-shaped boxes (206), and ends of the arc-shaped boxes (206) close to the drawer boxes (207) are bonded with rubber rings (208); piston strips (211) are slidably mounted at bottom ends inside the drawer boxes (207), sealing rings (212) are sleeved on outer sides of the piston strips (211), sound insulation plates (213) are bonded to top surfaces of the piston strips (211); and support strips (214) are uniformly distributed on sides of the sound insulation plates (213), nano silver films (215) are bonded to the other sides of the sound insulation plates (213), and sealing top plates (216) are bonded to top ends of the sound insulation plates (213); and voice boxes (217) are welded to ends of the drawer boxes (207), soft magnetic strips (218) are bonded to sides of the voice boxes (217) away from the drawer boxes (207), a magnetic attraction groove (219) is formed in a middle of one of the soft magnetic strips (218), and a magnetic attraction strip (220) is embedded in the other one of the soft magnetic strips (218) corresponding to the magnetic attraction groove (219); guide tubes (221) are welded to adjacent sides of the voice boxes (217) and the soft magnetic strips (218), aluminum strips (222) are slidably mounted inside the guide tubes (221), right-angle plates (223) are mounted at bottom ends of the aluminum strips (222), and suction cups (224) are embedded in middles of the right-angle plates (223); and a battery box (225) is mounted in a middle of a back surface of the arc-shaped back plate (1).

2. The hanging type intelligent voice input system for an ultrasonic report according to claim 1, wherein rotating shafts (204) are fixedly mounted inside the rotating grooves (202), the movable clamping plates (203) are movably sleeved on outer sides of the rotating shafts (204), ends of the rotating shafts (204) are movably clamped with extrusion cover plates (205), and sides of the extrusion cover plates (205) close to the movable clamping plates (203) are rough planes.

3. The hanging type intelligent voice input system for an ultrasonic report according to claim 1, wherein bottom ends of the aluminum strips (222) are curved in semicircular shapes, outer sides of the aluminum strips (222) are wrapped with polytetrafluoroethylene protective films, cross sections of the guide tubes (221) are hollow rectangles, and the outer sides of the aluminum strips (222) are attached to inner walls of the guide tubes (221).

4. The hanging type intelligent voice input system for an ultrasonic report according to claim 1, wherein pressure equalizing holes (209) are disposed at bottom ends of the arc-shaped boxes (206) close to the movable clamping plates (203), communication holes (210) are disposed at bottom ends of the drawer boxes (207) close to the arc-shaped boxes (206), and pick-up grooves (226) are disposed at middles of top ends of the drawer boxes (207).

5. The hanging type intelligent voice input system for an ultrasonic report according to claim 4, wherein auxiliary adjustment assemblies (3) are mounted on the arc-shaped back plate (1) and the fixing clamping plates (201), and the auxiliary adjustment assemblies (3) comprise mounting grooves (301);

mounting grooves (301) are disposed in middles of the fixing clamping plates (201), and folding airbags (302) are embedded inside the mounting grooves (301); air-filling and suction dual-purpose air pumps (303) penetrate through and are mounted in the middles of the fixing clamping plates (201), and inflation ends of the air-filling and suction dual-purpose air pumps (303) are connected to the folding airbags (302); and flexible ventilation tubes (304) are mounted at bottom ends of the fixing clamping plates (201), ends of the flexible ventilation tubes (304) are connected to the folding airbags (302), and the other ends of the flexible ventilation tubes (304) are connected to the pressure equalizing holes (209);

magnets (305) are embedded at the bottom ends of the fixing clamping plates (201), flexible sliding sleeves (306) are slidably sleeved in middles of the flexible ventilation tubes (304), and iron sheets (307) are bonded to bottom ends of the flexible sliding sleeves (306); cushion plates (308) are bonded to sides of the folding airbags (302), closed grooves (309) are disposed at bottom ends of the cushion plates (308), and ventilation holes (310) are disposed at top ends of the folding airbags (302) corresponding to the closed grooves (309); and closed strips (311) are slidably clamped in the closed grooves (309), the plurality of closed strips (311) are all connected to top surfaces of pulling plates (312), and cushion blocks (313) are uniformly bonded to sides of the cushion plates (308); and a buffer box (314) is bonded to a middle part of the arc-shaped back plate (1), adjusting holes (315) are disposed in a middle part of one side and two ends of the buffer box (314), and folding rubber tubes (316) are bonded inside the adjusting holes (315); elastic net cages (317) are bonded to sides of the folding rubber tubes (316) inside the buffer box (314), and breather holes (318) are evenly disposed in the folding rubber tubes (316) close to the elastic net cages (317) ; an internally threaded tube (319) is rotatably mounted in the middle part of the arc-shaped back plate (1), and one end of the internally threaded tube (319) penetrating through the buffer box (314) is connected to a threaded rod (320) through threads; and one end of the threaded rod (320) is located inside the buffer box (314) and is connected to a push plate (321) by welding, and buffer springs (322) are evenly distributed between the push plate (321) and the elastic net cages (317).

6. The hanging type intelligent voice input system for an ultrasonic report according to claim 5, wherein protective top plates (323) are bonded to top surfaces of the folding airbags (302), traditional Chinese medicine bags (324) are filled inside the elastic net cages (317), and an end cap (325) is movably clamped at a top end of the buffer box (314).

7. The hanging type intelligent voice input system for an ultrasonic report according to claim 5, wherein input ends of the voice boxes (217) and the air-filling and suction dual-purpose air pumps (303) are electrically connected to output ends of an external controller, and an input end of the controller is electrically connected to an output end of the battery box (225).

8. The hanging type intelligent voice input system for an ultrasonic report according to claim 5, wherein the system comprises an adjustment module, collection modules and a control processing module;

the adjustment module comprises the arc-shaped boxes (206), the drawer boxes (207), the piston strips (211), the folding airbags (302), the air-filling and suction dual-purpose air pumps (303) and the flexible ventilation tubes (304);

the collection modules are the voice boxes (217); and the control processing module is the external controller, and the external controller can be connected to wireless fidelity (WiFi) and Bluetooth for wireless operation.

9. The hanging type intelligent voice input system for an ultrasonic report according to claim 8, wherein the adjustment module comprises adjusting steps of:

inflating the folding airbags (302) by the air-filling and suction dual-purpose air pumps (303), inflating the arc-shaped boxes (206) through the flexible ventilation tubes (304), pushing the drawer boxes (207) to slide along the arc-shaped boxes (206) and eject, and allowing air to enter bottom ends of the drawer boxes (207) to eject the piston strips (211).

10. The hanging type intelligent voice input system for an ultrasonic report according to claim 9, wherein voice input by the collection modules is compared with online medical professional vocabulary data through the external controller, and the medical professional vocabulary is combined and input into a report.

* * * * *